United States Patent [19]

Kula et al.

[11] Patent Number: 5,523,223
[45] Date of Patent: Jun. 4, 1996

[54] KETOESTER REDUCTASE FOR CONVERSION OF KETO ACID ESTERS TO OPTICALLY ACTIVE HYDROXY ACID ESTERS

[75] Inventors: Maria-Regina Kula, Niederzier, Germany; Jörg Peters, Zürich, Switzerland

[73] Assignee: Forschungszentrum Julich GmbH, Julich, Germany

[21] Appl. No.: 284,600

[22] PCT Filed: Mar. 5, 1993

[86] PCT No.: PCT/DE93/00198

§ 371 Date: Aug. 11, 1994

§ 102(e) Date: Aug. 11, 1994

[87] PCT Pub. No.: WO93/18138

PCT Pub. Date: Sep. 16, 1993

[30] Foreign Application Priority Data

Mar. 13, 1992 [DE] Germany ............ 42 07 921.7

[51] Int. Cl.⁶ ............ C12N 9/02; C12N 9/04; C12P 7/62; C12P 7/26
[52] U.S. Cl. ............ 435/189; 435/135; 435/148; 435/190; 435/252.3; 435/255.4; 435/280; 435/921
[58] Field of Search ............ 435/191, 189, 435/135, 148, 190, 252.3, 255.4, 280, 921

[56] References Cited

U.S. PATENT DOCUMENTS 5,169,758 12/1992 Fischer et al. ............ 435/25

FOREIGN PATENT DOCUMENTS

| 3903759 | 2/1989 | Germany . |
| 56-160991 | 12/1981 | Japan . |
| 59-135889 | 8/1984 | Japan . |
| 64-86871 | 3/1989 | Japan . |
| 5146291 | 6/1993 | Japan . |
| 1044631 | 11/1981 | U.S.S.R. . |

OTHER PUBLICATIONS

Utting et al., J. Biol. Chem., vol. 250, No. 13, 5233–42, 1975.
Ward et al., Enzyme Microb. Technol., 1990, vol. 12.
Peters et al., Appl. Microbiol. Biotechnol., 38, 334–40, Dec. 1992.

Primary Examiner—David M. Naff
Assistant Examiner—Mike Meller
Attorney, Agent, or Firm—Herbert Dubno; Jonathan Myers

[57] ABSTRACT

A keto ester reductase capable of being used in an NADH-dependent enzymatic reaction for converting β, γ and δ ketonic acid esters into the corresponding optically active β, γ and δ hydroxycarboxylic acid esters can be isolated from strains of Candida parapsilosis, Yarrowinia cellobiosa, Rhodococcus erythropolis or Pseudomonas acidovorans, preferably cultivated on a long-chain alkane and/or alkane acid-containing culture medium, approximately in the presence of an inductor. The microorganism is preferably, Candida parapsilosis DSM 70125. A usable enzyme preparation can be recovered by fractionated PEG-precipitation from the cell raw extract: high specific activities (for example 1855 U/mg) may then be obtained by chromatographic purification. The keto ester reductase is characterized as having a molecular weight of 136 kDa+11 kDa as determined by gel permeation chromatography on Sephadex G-200, a pH optimum for conversion of the keto ester to the hydroxy acid esters between pH 7.8 and 8.0 and for the reverse reaction of converting the acid esters to the keto esters at a pH optimum of 9.5, and a temperature optimum between 36° and 40° C. for conversion of the keto esters to the hydroxy acid esters and from 50° to 56° C. for the reverse reaction of converting the acid esters to the keto esters. Not only (possibly substituted) so-called ketonic esters are accepted, but also number of other oxo-compounds among which diketones, (possibly substituted, in particular halogenated) aliphatic alicyclic and aromatic ketones, as well as ketoacetals and aldehydes. The S-enantiomer-forming reduction is supplemented by the possibility to recover R-enantiomers from racemates by oxidizing the S-enantiomer and separating the oxo-compound.

8 Claims, 7 Drawing Sheets

KETOESTER REDUCTASE FOR CONVERSION OF KETO ACID ESTERS TO OPTICALLY ACTIVE HYDROXY ACID ESTERS

DESCRIPTION

1. Field of the Invention

The subject of the invention is a new ketoester reductase suitable for NADH dependent enzymatic conversion of β-, γ- and δ-ketoesters to the corresponding optically active β-, γ- and δ-hydroxy acid esters and which is isolatable from strains of *Candida parapsilosis, Yarrowinia cellobiosa* or *Rhodococcus erythropolis* and *Pseudomonas acidovorans*.

2. Background of the Invention

Optically active β-, γ- and δ- hydroxycarboxylic acid esters are valuable chiral intermediates with wide application in the synthesis of pharmaceuticals, aromatic substances, pheromones, agrochemicals and enzyme inhibitors. They can only be obtained with difficulty in conventional chemical ways since the separation of the enantiomer mixtures resulting from chemical reduction is difficult and cost intensive.

The fermentative production of β-, γ- and δ-hydroxy carboxylic acids and esters with microorganisms is known. In these works the microbial cells are always introduced in excess and the yield and enantiomer excess of products vary over a wide range depending upon the source of the cells.

Primarily the bakers yeast *Saccharomyces cerevisiae* has been used.

There are already known oxidoreductases which are isolated from *Saccharomyces cerevisiae* which catalyze the enzymatic reduction of the β-, γ-and β-ketogroups from the corresponding ketoesters and the formation of the corresponding optically active hydroxy compounds (Heidlas et al (1988) Eur. J. Biochem, 172: 633–639). These known oxidoreductases require NADPH as coenzyme, which is difficult to regenerate so that this known enzymatic synthesis technique has not received commercial acceptance.

OBJECT OF THE INVENTION

The object of the invention is an enzymatic conversion of β-, γ- and δ- ketoesters catalyzed by an NADH dependent enzyme suitable therefor.

SUMMARY OF THE INVENTION

Such an enzyme has been surprisingly found in certain yeasts and bacteria and indeed in *Candida parapsilosis* and *Yarrowinia cellobiosa* as well as in *Rhodococcus erythropolis* and *Pseudomonas acidovorans* which are able to utilize n-alkane and n-alkanoic acids.

The ketoester reductase isolated from *Candida parapsilosis* and *Rhodococcus erythropolis* have been widely investigated.

Especially high activity of the new ketoester reductase (KERed) is obtained when *Candida parapsilosis* and *Rhodococcus erythropolis* are cultured on a nutrient medium which contains long-chain alkanoic acids or alkanes, especially dodecanoic acid and tetradecane as carbon sources.

The formation of the KERed with *Candida parapsilosis* DSM 70 125 and the isolation and purification of the enzyme from this strain has been especially intensively studied.

The purified KERed is characterized by the following parameters:

A pH optimum for the ketoester reduction between 7.8 and 8.0 and for the back reaction of pH 9.5.

A temperature optimum for the ketoester reduction between 36° C. and 40° C. and for the reverse reaction of 50° C. to 56° C.

Rapid deactivation by $Hg^{2+}$-, $Pb^{2+}$-, $Ag^{+}$-, $Cu^{2+}$-, $Ni^{2+}$, $Sn^{2+}$ and $Co^{2+}$ ions. Strong inhibition by p-hydroxymercuribenzoate, 5,5'-dithio-bis(2-nitrobenzoate) and iodoacetamide as well as by the chelators 2,2'-bipyridyl and o-phenanthroline. Stabilization with SH-protective reagents like dithiothreitol.

In addition the reduction of aliphatic alicyclic and aromatic ketones, diketones, ketals and aldehydes as well as the oxidation of primary and secondary alcohols are catalyzed.

The reductive enzymatic conversion of β-, γ-and δ-ketoesters to the corresponding optically active hydroxy carboxylic acid esters is effected according to the following equation:

R and R' can be various residues as will be apparent from Table 4. n can assume values of 1 to 3. Beyond that the model of the substrate binding site (FIG. 5, Table 5, Example 3.G) reaches the limits of the substrate acceptance.

Apart from the ketoesters, other oxocompounds are acceptable as substrates by the KERed as, for example, 1,1-dichloroacetone, chloroacetone, 3-chloro-2-butanone, 2-octanone, 2-butanone, 2-pentanone, 2-methyl-3-pentanone, methoxy-2-propanone, acetophenone, 3-chloroacetophenone, 4-fluoroacetophenone, 4-bromoacetophenone, propiophenone, 2,4-hexanedione, 2,4-pentanedione as well as acetaldehyde, isobutyraldehyde and propionaldehyde. Acetophenone is converted to (S)-phenylethanol, 3-oxobutyric acid ethyl ester to (S)-3-hydroxybutyric acid ethylester and 5-oxohexanoic acid ethyl ester to (S)-5 hydroxyhexanoic acid ethyl ester.

In this connection the possibility of converting acetophenone, 4-bromoacetophenone, 3-chloroacetophenone and 4-fluoroacetophenone to the corresponding (S)-phenylethanol in NADH-dependent catalysis is especially interesting since up to now only (R) specific transformations could be realized.

The reverse reaction (oxidation of the hydroxy group) can also be carried out enzymatically and can especially be used to recover the desired R enantiomer if desired from a racemate of R- and S hydroxy compounds by conversion of the S-enantiomer to the oxo compound.

The ketoester reductase which will be described in detail, is, as has been indicated, not only suitable for the reduction of the β-, γ-and ε- keto groups of the ketoesters, but beyond that can be used for the reduction of a wide range of carbonyl compounds. Consequently, the enzyme can also be characterized as a carbonyl reductase.

The new enzyme can be categorized under the Number EC 1.2.1 of the EC classification. The exact establishment of an EC number has not occurred as yet. For simplicity, the new enzyme is referred to as a ketoester reductase (KERed).

One obtains the KERed in a manner known per se by cultivation (in usual nutrient media optionally in the presence of alkanes and/or alkanoic acids) of the named microorganisms from whose crude extracts a usable enzyme preparation is obtained by fractional PEG precipitation, in which the polyethyleneglycol (PEG) with relatively low molecular weight is used to precipitate other proteins while the KERed remains in solution. The KERed is then precipitated from the supernatant by PEG of higher molecular weight and is further resolubilized from the precipitate by buffer solution.

Alternatively, one can operate with different PEG concentrations but the same molecular weight in the range of 1,000–10,000, especially about 5,000. A further purification by chromatographic separation methods results in a preferred isolate with higher specific activity as will be apparent from the following examples.

BRIEF DESCRIPTION OF THE DRAWINGS

In the following, the invention will be described in greater detail with reference to examples. Reference is made to the accompanying drawings.

a) 5.4% glucose, b) 0.8% glucose, c) 2% glycerine d) 2% glycerine +0.1% inductor, e) 1% dodecanoic acid, f) 1 dodecanoic acid and 0.1% inductor; inductor: 3-oxohexanoic acid ethyl ester.

EXAMPLE 1: Recovery of the Enzyme

1. Screening

For screening collection strains of the DSM (German Collection of Microorganisms and Cell Cultures, Braunschweig) is cultured in the DSM recommended medium, the cell mass is harvested by centrifugation and disintegrated by wet milling. A permanent deposit of *Candida parapsilosis* DSM 70125 has been deposited on 29 Mar. 1979 in accordance with the requirements of the Budapest Treaty. The address of the depository is as follows: German Collection of Microorganisms and Cell Cultures, DSM-Mascheroder Weg 1B, Braunschweig, Germany. The supernatant served as the enzyme source (crude extract) and was investigated for ketoester reductase activity. The test was carried out photometrically and the test mixture contained the following components.

0.2 mM NAD(P)H
8 mM ketoester
0.1M triethanoleamine (TEA)-NaOH-Buffer, pH 7
Limited amounts of the crude extract.

The NAD(P)H-decrease at 334nm over a period of 1 minute was followed: For activity calculation, an absorption coefficient of $6.18 M^{-1} cm^{-1}$ was used. Table 1 summarizes the obtained specific activity for the individual microorganisms which were found to be useful out of a group of 65 strains. For each microorganism, the NADH dependent activity is given in the first column, in the second column, the NADPH-dependent specific activity is given in mU/mg protein. One U (unit) corresponds to the consumption and conversion of 1 µmole of reduced coenzyme per minute.

TABLE

| KERed from: | AEEE[1] | BEEE | ABS | ABEE | LS | LSEE |
|---|---|---|---|---|---|---|
| | | | mU/mg | | | |
| *P. acidovorans* | 49.0 | 11.6 | 9.1 | 15.9 | —[2] | 4.1 |
| | — | 15.6 | 3.5 | — | — | — |
| *R. erythropolis* | 153.0 | 3.0 | n.b.[3] | 97.0 | n.b. | 87.1 |
| | — | — | n.b. | — | n.b. | — |
| *C. parapsilosis* | 91.0 | 49.0 | 16.4 | 96.1 | 2.7 | 85.1 |
| | 14.1 | 25.0 | 25.0 | 4.5 | 2.4 | 1.3 |
| *Y. cellobiosa* | 103.1 | 20.3 | n.b. | 55.4 | n.b. | 41.1 |
| | 5.0 | — | n.b. | — | n.b. | 4.0 |

[1] AEEE: acetoacetic acid ethyl ester; BEEE: butyrylacetic acid ethyl ester; ABS: Acetylbutyric acid; ABEE Acetylbutyric acid ethyl ester; LS: levulinic acid; LSEE: levulinic acid ethyl ester;
[2] —: Activity below detection limit;
[3] n.b.: not determined.

2. Cultivation of *Candida parapsilosis*

For the enzyme recovery, *Candida parapsilosis* is cultivated in the following medium per one liter of:

| Yeast extract | 10 g |
|---|---|
| Potassium phosphate | 1 g |
| Ammonium sulfate | 1.2 g |
| Glycerine | 20 g (not repressed) |
| or Glucose | 54 g (repressed) |
| or Glucose | 8 g (depressed) |
| or Dodecanoic acid | 10 g | optionally 0.1% addition of 3-oxohexanoic acid ethyl ester (inductor)

Figure 1:
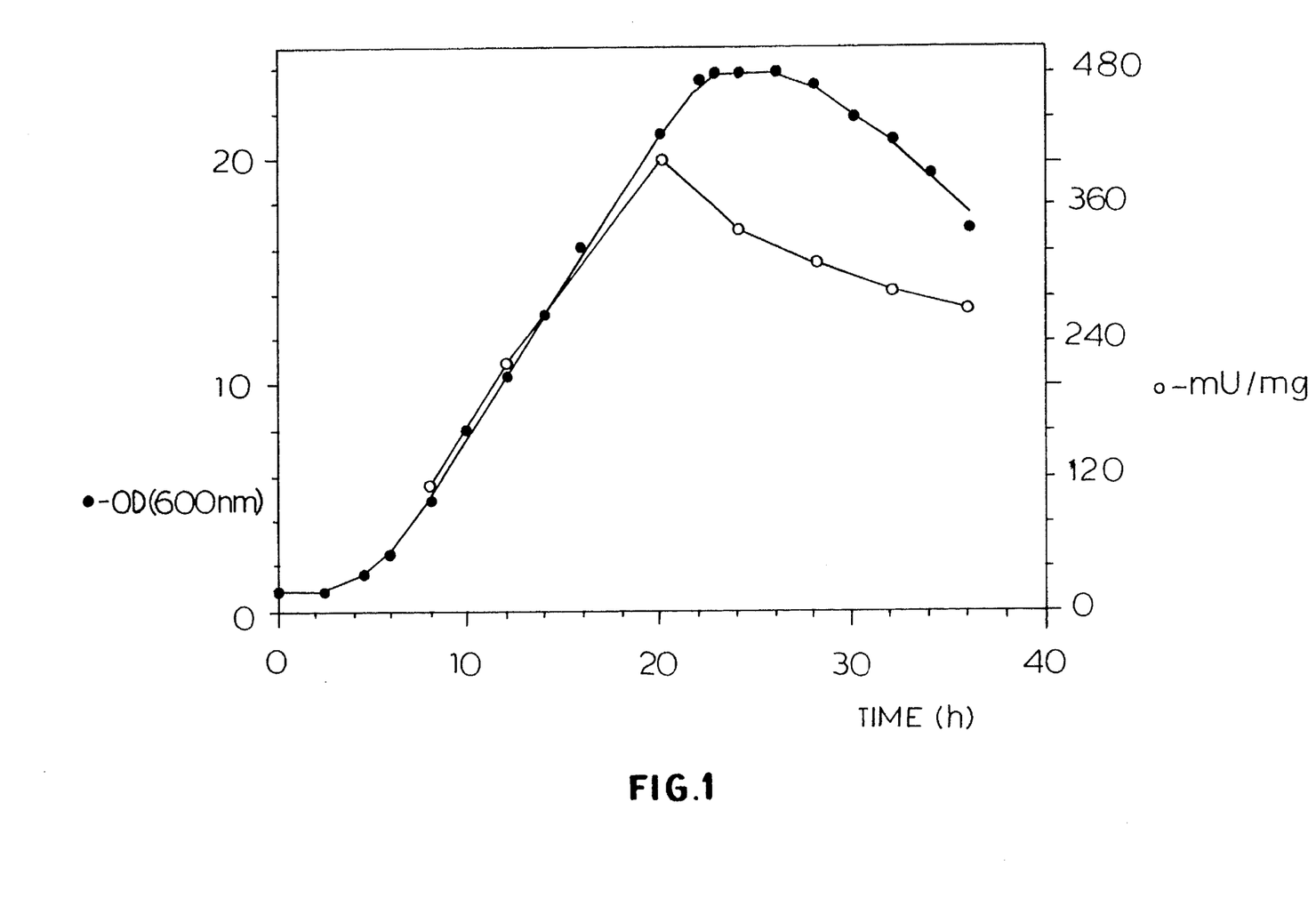
FIG. 1 and FIG. 2 show the formation of the KERed by means of *Candida parapsilosis* upon cultivation on glycerine (1) or dodecanoic acid (2) with respect to time.
Figure 2:
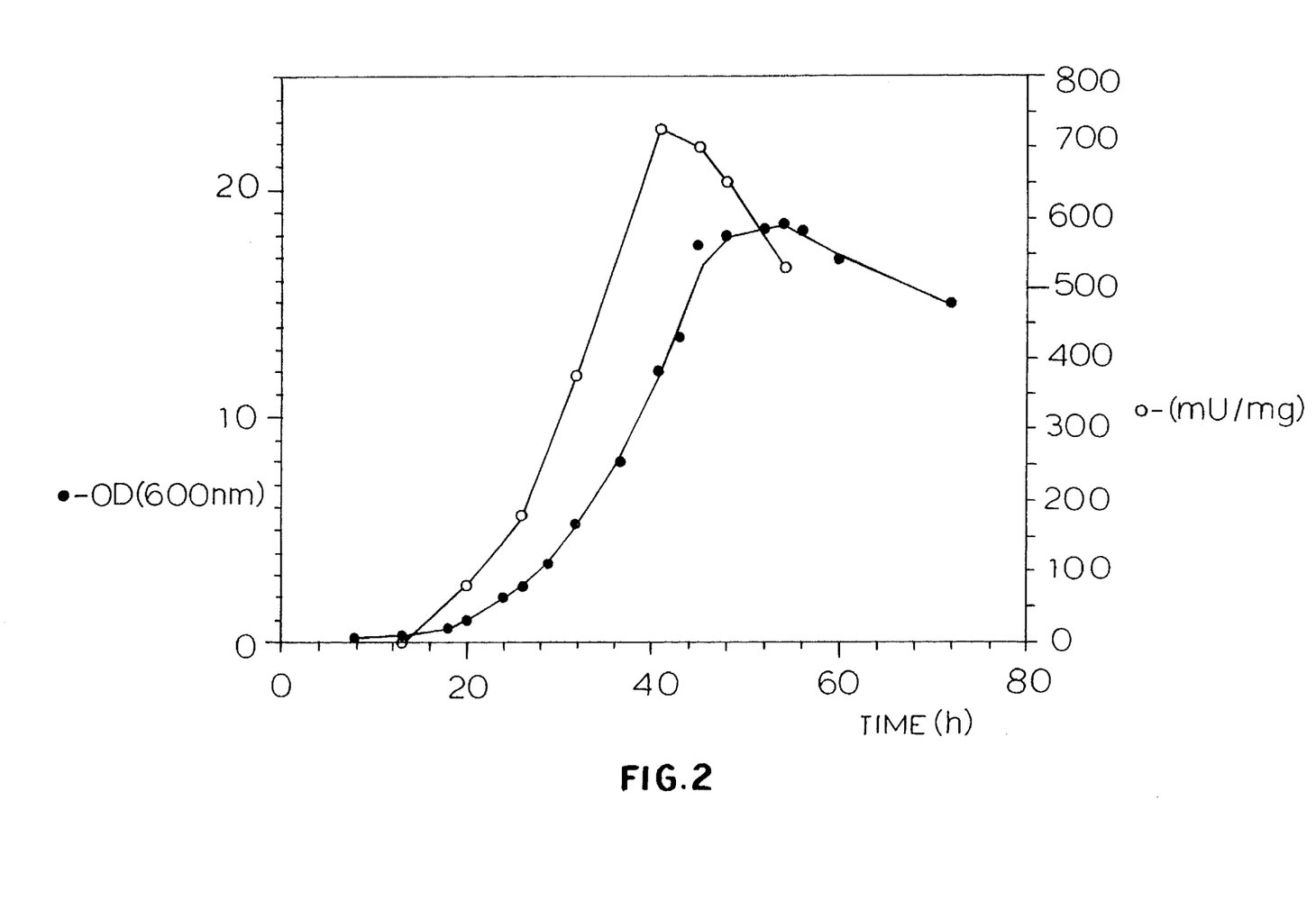

The pH value of this solution was adjusted to 4.5 and it was then sterilized for 15 minutes at 121° C. (2 bar). The organism was aerobically cultivated. In 10 l scale, the medium after reaching the incubation temperature of 30° C. was inoculated with 400 ml of a 20 hour old preculture. In one such 10 liter batch the course of the enzymatic activity over time was determined by removing samples at different times determining the activity of the keto ester reductase after the disintegration of the cells. In FIG. 1 such a course has been illustrated, the activity of the ketoester reductase reaches a maximum at 20 hours and decreases thereafter. The cell harvest was effected after 20 hours by centrifugation at which 175 g of moist biomass was obtained from 8 liters of medium. The cell mass can be stored frozen at −20° C. whereby no loss in activity can be observed over several weeks.

3. Enzyme isolation (crude extract)

The enzyme liberation from the whole cells can be carried out by methods known per se (ultrasound, high pressure homogenization, wet milling, etc.). Here the cells are broken by wet milling with glass beads. For this the cell mass (175 g) is suspended in the disintegration position buffer (200 mM TEA-NaOH-buffer (pH 7.5) with the addition of 5 mM dithiothreitol and 1 mM of protease inhibitor (Pefablock of the Company Merck, Darmstadt) so that the concentration of the moist cell mass is 25% (700 ml final volume).

The cell contents were liberated from the cooled suspension (4° C.) by mechanical disintegration with the aid of a glass bead mill (Disintegrator S from the Company IMA, Frankfurt). The milling container is filled with glass beads (0.5 mm:0.3 mm=2:1 ratio, 90 ml) and with 60 ml of the 25% cell suspension. The disintegration is carried out with a stirring speed of 4000 RPM. The cooling jacket was cooled during the run. A disintegration time of 9 minutes was found to be optimal and was used for the disintegration of the cells. Following the cell disintegration, the supernatant was decanted and the glass beads washed twice with disintegration buffer.

175 g of the moist yeast mass give 285 ml of crude extract with a volumetric activity of 6.6 u/ml and a protein content of 10.7 mg/ml. From this it was calculated that from 100 l of fermenter volume about 23000 units of ketoester reductase can be recovered (1 enzyme unit is the enzyme quantity of enzyme required to transform 1 μmol of acetylbutyric acid ethyl ester per minute).

4. Enrichment of the Enzyme

The enzyme can be enriched and purified by methods known per se for protein purification like two-stage fractional polyethyleneglycol precipitation, ion-exchange chromatography and affinity chromatography.

4.1 Fractional polyethyleneglycol precipitation

Ice-cooled crude extract (4° C.) is reacted with stirring and pH control (pH 7–7.5) with polyethyleneglycol ($M_w$: 5000) until it reached a concentration of 4% (w/v). After centrifugation at 10000 RPM, the supernatant is treated with $PEG_{5000}$ until a final concentration of 30% is reached. The sediment following centrifugation at 10,000 RPM for 15 minutes contains the ketoester reductase activity and can be taken up in triethanolamine-NaOH buffer, pH 7.5, and lyophilized. The enzyme can be kept under these conditions for several months without activity loss.

4.2 Ion-exchange chromatography 1 ml of resuspended sediment from the 30% PEG precipitation (corresponding to Example 4.1), was applied to a Q-sepharose fast flow column (anion exchanger, HiLoad, high performance, 16/10, 20 ml gel volume) (FPLC-Chromatography system of the Company Pharmacia, Freiburg).

The column is equilibrated with buffer A (20 mM triethanolamine-NaOH-buffer; pH 7.5). After abundant washing of the column with buffer A, the ketoester reductase is eluted with a linear NaCl gradient (0–200 mM) whereby the enzyme is eluted out at about 100 mMNaCl. The chromatography is carried out at a flow rate of 1 ml/min. The resulting enrichment is summarized in Table 2.

4.3 Affinity chromatography

The fractions of the Q-sepharose chromatography with the highest activity were collected, concentrated with the aid of an ultrafiltration cell (Amicon, Witten/Ruhr) and further purified by chromatography on agarose-NAD (Sigma, Deisenhofen). The low pressure chromatography system of Pharmacia was used. The gel bed amounted to 5 ml. The chromatography was carried out at a flow rate of 0.5 ml/min. The enrichment is summarized in Table 2.

TABLE 2

Purification of the ketoester reductase

| Purification Step | Spec. Activity (U/mg) | Total Yield (%) | Enrichment (times) |
|---|---|---|---|
| Crude extract | 0.6 | 100 | 1.0 |
| 4% PEG-precipit. | 0.7 | 75 | 1.2 |
| 30% PEG-precipit | 2.5 | 75 | 4.2 |
| Q-sepharose FF | 40.3 | 71 | 67.0 |
| Ultrafiltrtion | 40.3 | 67 | 67.0 |
| Agarose-NAD$^+$ | 1855.0 | 67 | 3091.0 |

The apparent native molecular weight of the ketoester reductase of 136 kDa (±11 kDa) was determined by gel permeation chromatoraphy on Sephadex G-200. Thyroglobulin, ferritin, catalase, aldolase, bovine serum albumin, ovalbumin, chymotrypsinogen A and ribonuclease A served as standardizing proteins. The two identical large subunits have an apparent molecular weight of 67 kDa as was determined by SDS gel electrophoresis. The molecular weight standard was a mixture of $\alpha_2$-macroglobulin, phosphorylase b, bovine serum albumin, glutamate dehydrogenase, lactate-dehydrogenase and trypsin inhibitor.

Depending upon the different origns of the KERed, certain deviations in molecular weight with identical function (NADH-dependent reduction of β-,γ-and δ- ketoesters) can be expected.

EXAMPLE 2: Regulation of the Ketoester Reductase

The regulation of the ketoester reductase was investigated, for this purpose, cells were cultivated on different C-sources (see Example 1; 2) in 200 ml scale. The point in time at which the activity of the ketoester reductase reached a maximum was determined and was established as the harvest time point (see FIG. 1).

Figure 3:
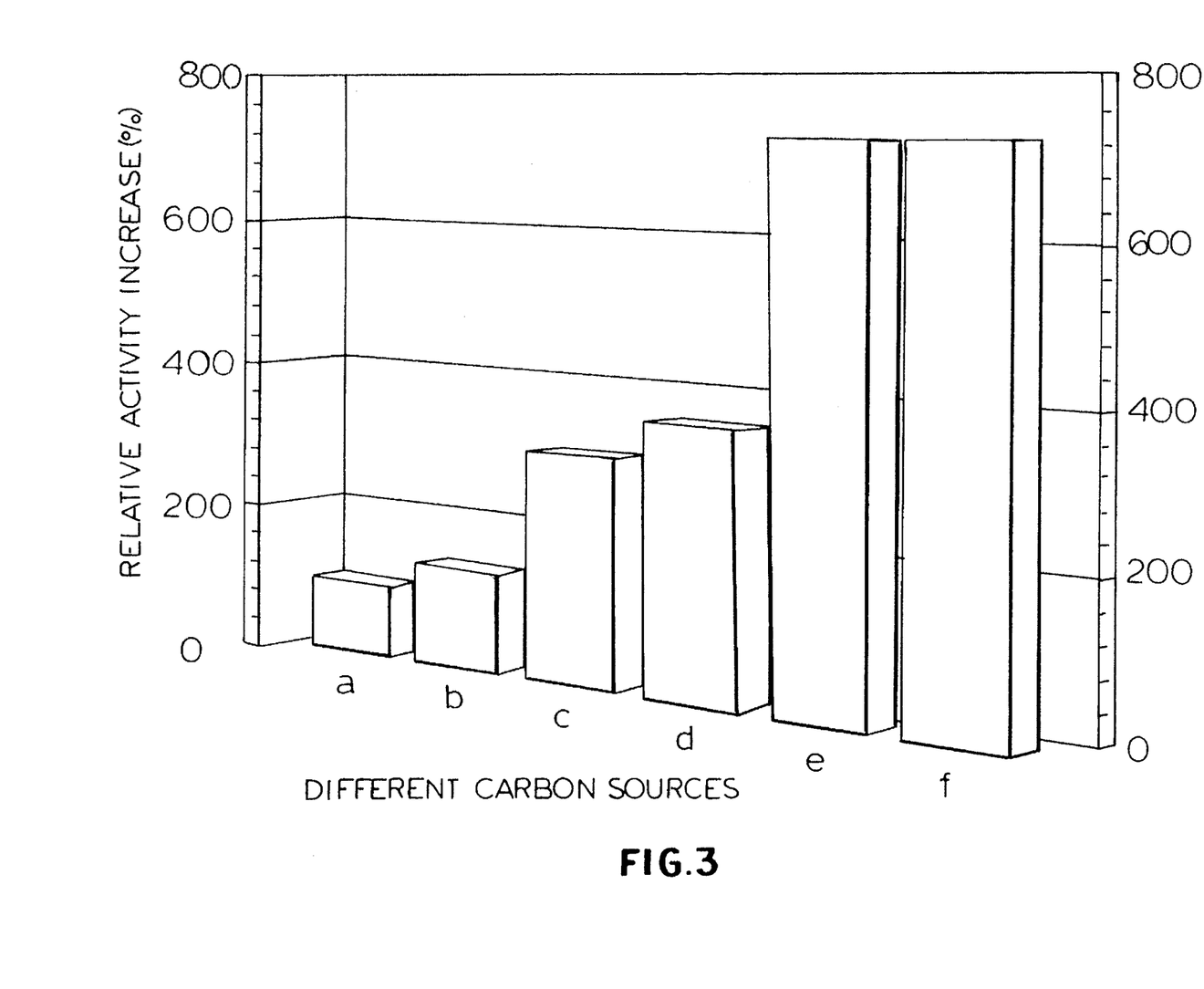
FIG. 3 shows the regulation of the activity of the KERed from *Candida parapsilosis* with respect to the following carbon sources.

The specific activity of the ketoester reductase for 3-oxohexanoic acid ethyl ester is shown in FIG. 3 in dependence upon the growth on different C-sources. The ketoester reductase of *Candida parapsilosis* underlies the catabolite repression. Under derepressed conditions (0.8% glucose in the medium) the specific activity of the enzyme is about 36% higher than under repressed conditions (5.4% glucose in the medium). Under nonrepressed conditions (2% glycerine in the medium) the specific activity is about 300% higher than under repressed conditions. With growth on dodecanoic acid, the activity of the ketoester reductase of *Candida parapsilosis* was increased to above 700%. The addition of a ketoester to the medium (0.1%) yields in the case of glycerin as a C-source, an increase of the specific activity to 350%.

EXAMPLE 3: Characterization of the ketoester reductase

For the following investigation, partially purified enzyme (after Q-sepharose chromatography, 67-times enrichment) was used.

A. pH-Dependency of the Conversion

Figure 4:
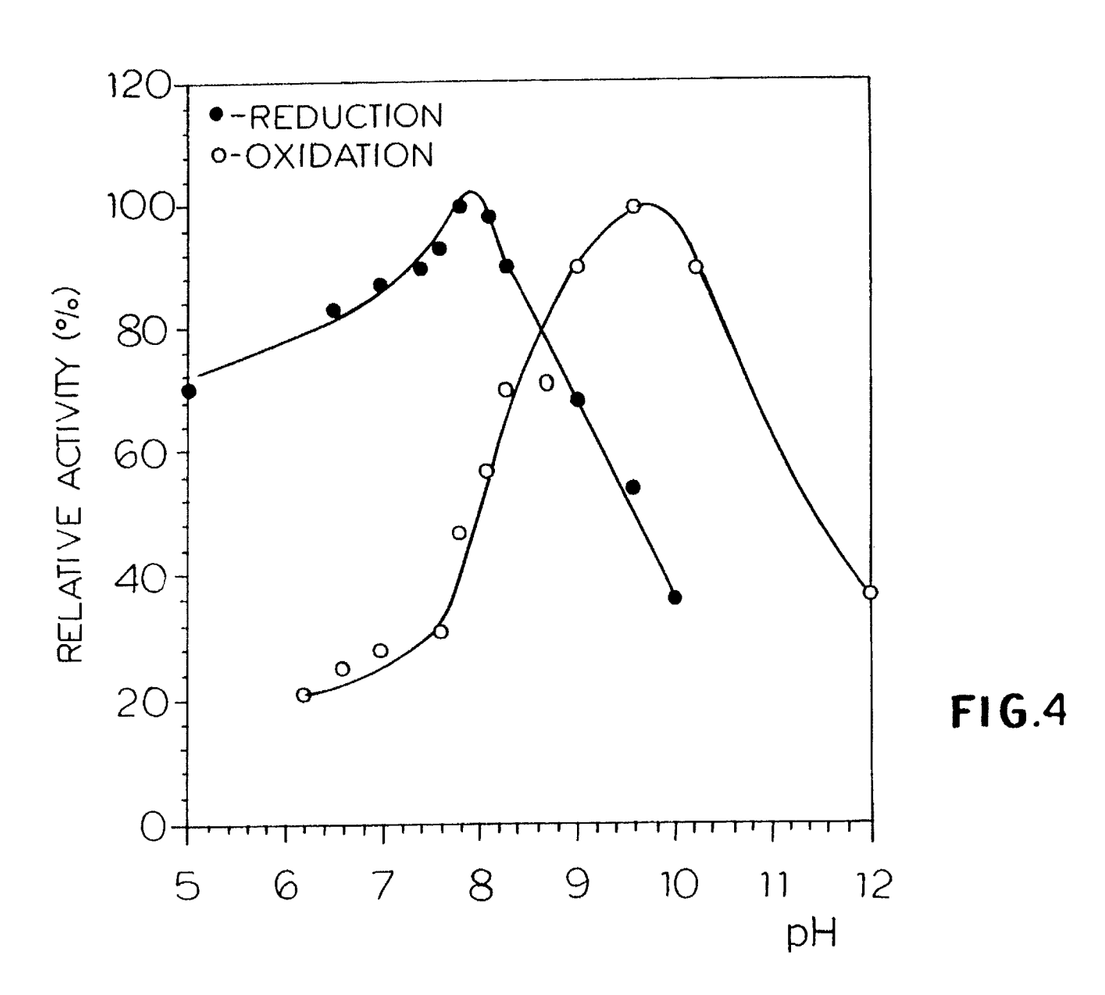
FIG. 4 shows the pH dependency of the KERed activity on oxidation and reduction

The dependency of the activity upon the pH value was determined by mixing 5-oxohexanoic acid ethyl ester (35 mM) with NADH (0.2 mM) and 1.0 μl of enzyme solution at different pH values (0.2M buffer solution) and following the activity at 340 nm (30° C.) photometrically. FIG. 4 shows the obtained activity values in dependence upon pH value, the optimum for the reduction of 5-oxohexanoic acid ethyl ester lying at pH 7.9.

In analogous ways, the pH optimum for the reverse reaction, the 5-hydroxyhexanoic acid ethyl ester oxidation, was measured. (R/S)-5-hydroxy hexanoic acid ethyl ester (35 mM) was dissolved in 0.2M buffer with pH values between 4 and 10, 0.2 mM NAD and 10 μl enzyme solution was added and the NADH-formation rate photometrically followed at 340 nm. FIG. 4 records the obtained values, the pH optimum for the oxidation lying at pH 9.5.

B. Temperature dependency of the Reduction

To determine the optimum temperature of the reduction, the enzymatic activity was measured between 30° and 60° C. The test composition contained:

| | |
|---|---|
| 5-oxohexanoic acid ethyl ester | 35 mM |
| NADH | 0.2 mM |
| Enzyme solution | 10 μl |
| TEA-NaOH-buffer, 0.1 M; pH 7.9 | |

The KERed from *Candida parapsilosis* had a temperature optimum for the reduction between 36° and 40° C.

C. Temperature optimum of the Oxidation

To determine the temperature optimum of the oxidation, the enzymatic activity between 30° C. and 60° C. was measured. The test composition contained:

| | |
|---|---|
| 5-Hydroxyhexanoic acid ethyl ester | 35 mM |
| NAD | 0.5 mM |
| Enzyme solution | 10 μl |
| TRIS-HCl-buffer, 0.1 me pH 9 | |

The KERed from *Candida parapsilosis* had a temperature optimum for the oxidation between 50° and 56° C.

D. Influence of Various Reagents upon the KERed

The influence of various metal cations and reagents upon the enzymatic activity was investigated in tests in which the test preparation described under example 3.B was used.

The results of the inhibition studies are assembled in Table 3. It is noticible that the enzyme is relatively strongly inhibited by the chelator o-phenanthroline, but is practically not inhibited by EDTA by contrast. Apparently the ketoester reductase requires an essential metal ion which is removed by o-phenanthroline but not EDTA, which leads to the activity loss. The progressively stronger inhibition of the ketoester reductase by thiol reagents like N-ethylmaleimide, iodoacetamide, 2,2-dithio-bis( 2-nitrobenzoate) and p-hydroxymercuribenzoate indicates that the enzyme contains at least one essential SH group.

TABLE 3

Inhibition Study of the KERed from *C. parapsilosis*

| Compound | Residual Activity [%] | |
|---|---|---|
| | 0.1 mM | 1.0 mM |
| Metal ions | | |
| $Hg^{2+}$ | 0 | 0 |
| $Pb^{2+}$ | 0 | 0 |
| $Ag^+$ | 0 | 0 |
| $Cu^{2+}$ | 0 | 0 |
| $Ni^{2+}$ | 10 | 0 |
| $Zn^{2+}$ | 24 | 0 |
| $Sn^{2+}$ | 73 | 0 |
| $Co^{2+}$ | 38 | 12 |
| $Ca^{2+}$ | 78 | 68 |
| $Mn^{2+}$ | 84 | 80 |
| $Mg^{2+}$ | 91 | 82 |
| $Fe^{3+}$ | 100 | n.b.[1] |
| KCN | 100 | 100 |
| Chelators | | |
| EDTA (1 mM, 10 mM) | 100 | 80 |
| 2,2'-bipyridyl (0.05 mM; 0.5 mM) | 52 | 23 |
| o-Phenanthroline | 26 | n.b. |
| Sulfhydryl-Reagents | | |
| p-Hydroxymercuribenzoate | 0 | 0 |
| 5,5'-dithio-bis (2-nitrobenzoate) | 53 | 0 |
| Iodoacetamide | 77 | 17.5 |
| N-ethylmaleimide | 70 | 47 |
| Methylglyoxal | 100 | 34 |
| Sulfhydryl-Protective Reagents | | |
| 1,4-Dithiothreitol | 100 | 100 |
| Glutathione (reduced) | 100 | 100 |
| Histidine-specific reagents | | |
| Diethyl Pyrocarbonate | 100 | 100 |
| Other Reagents | | |
| Ethanol (5%) | — | 30 |
| Triton X-100 (0.1%) | — | 100 |
| Pefabloc (Protease Inhibitor) | n.b. | 100 |

[1] n.b.: not determined

E. Influence of the Buffer Concentration on the Activity of the FaRed

The influence of the buffer concentration on the activity of ketoester reductase was tested. The test composition in example 3.B was used with variation of the buffer concentration.

The enzymatic activity is maximal at a concentration of the buffer of 0.1M.

F. Substrate spectrum of the KERed

Corresponding to example 3.B, instead of 5-oxohexanoic acid ethyl ester a series of aromatic and aliphatic ketoesters, ketoacids, ketones, diketones and aldehydes were investigated as to whether they could be reduced enzymatically. For this the compounds were added always in 8 mM final concentration. The results are collected in Table 4. It indicates that the enzyme accepts a multiplicity of aromatic and aliphatic compounds as substrate. The activity with 5-oxohexanoic acid ethyl ester was arbitrarily selected as 100%.

TABLE 4

Substrate specificity of the KERed from *C. parapsilosis*

| Compound | Rel. Activity [%] | Compound | Rel. Activity [%] |
|---|---|---|---|

Keto acids and esters

| Compound | Rel. Activity [%] | Compound | Rel. Activity [%] |
|---|---|---|---|
| methyl acetoacetate | 67 | ethyl acetoacetate | 76 |
| ethyl acetoacetate | 61 | tert-butyl acetoacetate | 137 |
| 4-oxopentanoic acid | 0 | ethyl 4-oxopentanoate | 76 |
| ethyl 4-oxohexanoate | 100 | 4-oxohexanoic acid | 0 |
| ethyl 4,4,4-trifluoroacetoacetate | 21 | ethyl 4-chloroacetoacetate | 92 |
| methyl 3-oxopentanoate | 18 | ethyl 3-oxopentanoate | 32 |
| ethyl 3-oxohexanoate | 51 | ethyl 4,4-dimethyl-3-oxopentanoate | 24 |
| ethyl benzoylacetate | 0 | ethyl 2-methylacetoacetate | 70 |

Diketone

| Compound | Rel. Activity [%] | Compound | Rel. Activity [%] |
|---|---|---|---|
| 2,4-pentanedione | 15 | 2,4-hexanedione | 46 |
| 2,5-hexanedione | 46 | isatin | 0 |
| 1,3-cyclohexanedione | 0 | | |

Alicyclic Ketone

| Compound | Rel. Activity [%] | Compound | Rel. Activity [%] |
|---|---|---|---|
| 4-methylcyclohexanone | 40 | 2-methylcyclohexanone | 12 |

TABLE 4-continued

Substrate specificity of the KERed from *C. parapsilosis*

| Compound | Rel. Activity [%] | Compound | Rel. Activity [%] |
|---|---|---|---|
|  | 16 | | |
| *Aromatic Ketone* | | | |
|  | 34 |  | 0 |
|  | 35 |  | 40 |
|  | 40 |  | 0 |
| *Aliphatic Ketone* | | | |
|  | 51 |  | 60 |
|  | 105 |  | 53 |
|  | 28 |  | 51 |
|  | 48 |  | 40 |
|  | 54 |  | 33 |
|  | 0 |  | 4 |
|  | 118 |  | 14 |
| *Aliphatic Aldehyde* | | | |
|  | 150 |  | 127 |

TABLE 4-continued

Substrate specificity of the KERed from C. parapsilosis

| Compound | Rel. Activity [%] | Compound | Rel. Activity [%] |
|---|---|---|---|
|  | 178 |  | 29 |

α-ketocarboxylic acid and esters and allyl-ketones were not converted.

As one can see, the substrate spectrum of the ketoester reductase is extremely broad, whereby apart from β-, γ- and δ-ketoesters, 1, 3- and 1,4-diketones, optionally substituted and especially halogenated aliphatic, allcyclic and aromatic ketones, ketoacetals and aldehydes are accepted.

G. Kinetic Characterization of the KERed

Using the above described photometric tests, the kinetic constants of selected substrates of the KERed from *Candida parapsilosis* were measured. The results of the kinetic characterization are summrized in Table 5.

TABLE 5

Kinetic Characterization of the KERed

| No. | Substrate | $V_{max}$ (%) | $K_m$ (mM) | $V_{max}/K_m$ (—) |
|---|---|---|---|---|
| | Aliphatic Ketone | | | |
| 1. | Acetone | 97 | 1.060 | 5.5 |
| 2. | Chloroacetone | 61 | 0.124 | 29.5 |
| 3. | 1,1-Dichloroacetone | 45 | 0.176 | 15.3 |
| 4. | Pyruvaldehyde-Dimethyl-acetal | 24 | 0.189 | 7.6 |
| 5. | 2-Butanone | 100 | 1.480 | 4.1 |
| 6. | 3-chloro-2-butanone | 50 | 0.442 | 6.8 |
| 7. | 2-pentanone | 62 | 0.141 | 26.4 |
| 8. | 2-hexanone | 53 | 0.054 | 58.9 |
| 9. | 3-hexanone | 10 | 0.840 | 0.7 |
| 10. | 2-heptanone | 58 | 0.097 | 35.9 |
| 11. | 3-heptanone | 11 | 5.6 | 0.1 |
| 12. | 4-heptanone | 9 | 5.3 | 0.1 |
| 13. | 2-octanone | 62 | 0.324 | 11.5 |
| 14. | 3-octanone | 12 | 11.20 | 0.1 |
| 15. | 2-nonanone | 45 | 0.314 | 8.6 |
| 16. | 2-decanone | 20 | 3.960 | 0.3 |
| | Aromatic ketones | | | |
| 17. | Acetophenone | 22 | 0.049 | 26.9 |
| 18. | 3-chloro-aceto-phenone | 32 | 0.015 | 128.0 |
| 19. | 4-chloro-acetophenone | 19 | 0.010 | 114.0 |
| | Aldehyde | | | |
| 20. | Acetaldehyde | 129 | 0.085 | 91.0 |
| | Ketoesters | | | |
| 21. | Ethyl 3-oxo-butanoate | 79 | 0.122 | 38.9 |
| 22. | Tert.-Butyl 3-oxo-butanoate | 71 | 0.356 | 12.0 |
| 23. | Ethyl 4-chlor-3-oxo-butanoate | 10 | 3.56 | 0.2 |
| 24. | Ethyl 4-trifluor-3-oxo-butanoate | 11 | 2.0 | 0.3 |
| 25. | Ethyl 3-oxopentanoate | 17 | 6.9 | 0.1 |
| 26. | Ethyl 3-oxohexanoate | 5 | 1.3 | 0.2 |
| 27. | Ethyl 4-oxopentanoate | 12 | 1.73 | 0.4 |
| 28. | Ethyl 5-oxohexanoate | 116 | 0.89 | 7.8 |
| 29. | Methanol | | No Reaction | |
| 30. | Ethanol | 42 | 3.4 | 0.7 |
| 31. | 1-propanol | 47 | 3.8 | 0.7 |
| 32. | 1-butanol | 47 | 2.9 | 1.0 |
| 33. | 2-propanol | 183 | 2.21 | 5.0 |
| 34. | (S)-2-butanol | 210 | 0.6 | 21.0 |
| | Coenzyme | | | |
| 35. | NADH | 105 | 0.038 | 165.8 |
| 36. | NADPH | | No Reaction | |

All $V_{max}$ values are referred to 2-butanone (6U mg, partially purified enzyme) substrate inhibition was observed with chloroacetone (($K_{is}$: 121.3 mM), 3-hexanone ($K_{is}$: 612 mM) and 2-nonanone ($K_{is}$ 24.9 mM). In general the standard deviation of the maximum reaction rate and the Michaeli-Menten-Constant fell between 5 and 10% of the values.

Figure 5:
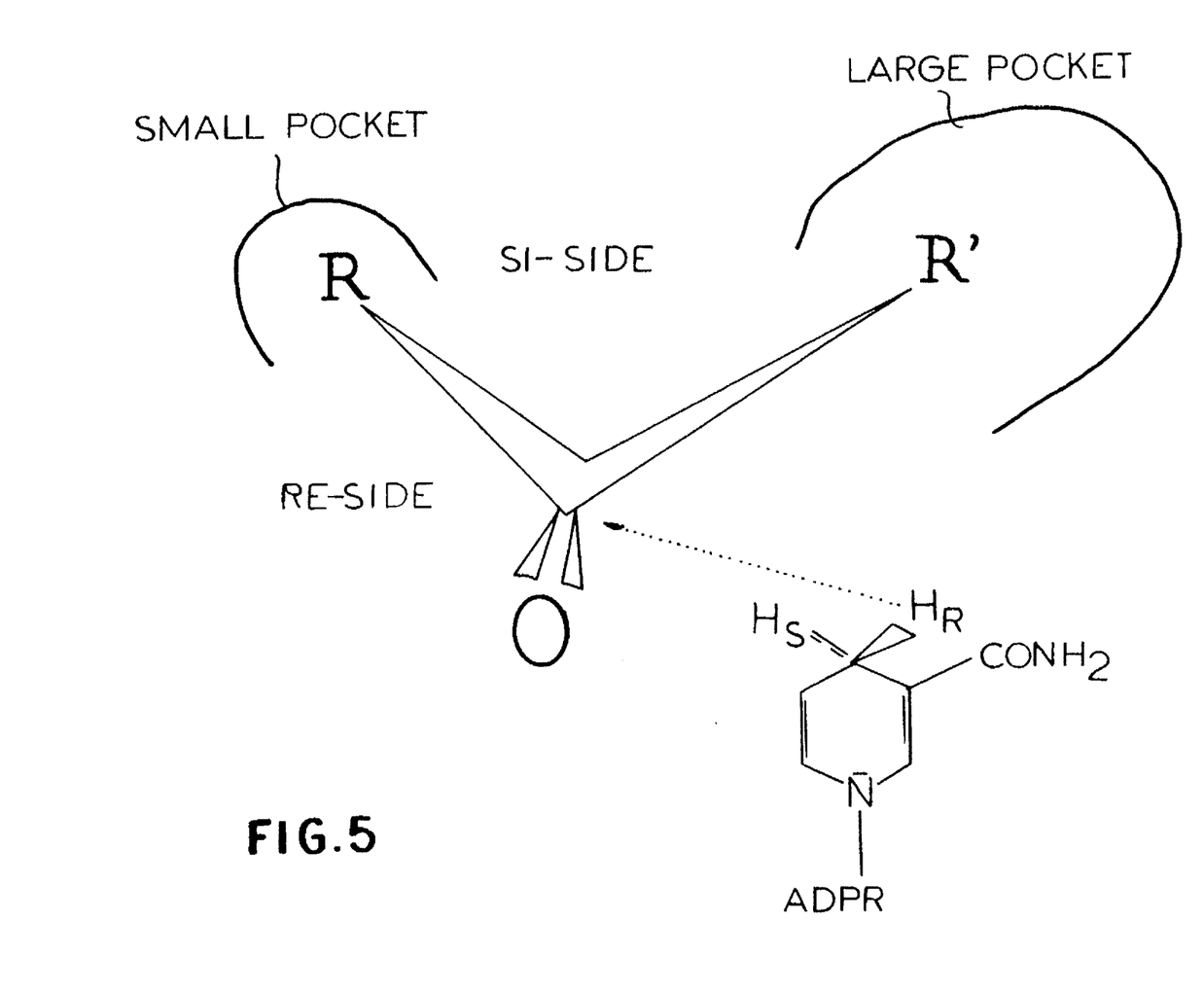
FIG. 5 shows a model of the substrate binding site of the KERed of *Candida parapsilosis*.

From these results, a model for the substrate binding site of the KERed can be obtained. From this model it is possible to predict whether a given potential substrate will be accepted by the KERed or not. In FIG. 5 the model of the substrate binding site is shown. From this the substrate binding site is comprised of two regions which differ with respect to volume and hydrophobicity. The smaller pocket can receive methyl, ethyl, and propyl groups and further, substituted methyl groups like, e.g. the chloromethyl group, can also be accepted. The larger pocket can bind long and hydrophobic residues. As is apparent from Table 5, these aliphatic residues can be up to $C_8$ (see 2-decanone). The larger pocket can also receive a multiplicity of sterically fastidious residues and determines considerably the unusually broad spectrum of the enzyme.

H. Enzyme Catalyzed production of 3-hydroxybutyric acid methyl ester in a Batch Conversion A solution of 3-oxobutyric acid methyl ester (100 mM) is incubated with ketoester reductase (10 U) and coenzyme (0.1 mM) (100 ml total volume), whereby the coenzyme NADH is regenerated by coupling with sodium formiate (1M) and formiate dehydrogenase (40 U). At uniformly spaced intervals, samples were removed and analyzed by thin layer chromatography (DC) for the 3-hydroxybutyric acid methyl ester. The enantiomeric purity was determined by GC analysis.

Separating conditions of the DC:

Stationary phase: silica gel 60 F254

Mobile phase: diethylether: petrolether$_{60-80}$=2:1

Path length: 5 cm

Immersion solution: 10% molybdatophosphoric acidhydrate solution in ethanol (absolute) with 4% HCl Process: Ascending chromatography with chamber saturation Sample volume: 2–10 μl Separation Behavior: hydroxy acid/ester travels less far than ketoacid/ester After the reaction time of 30 hours had lapsed, the reaction mixture was extracted with chloroform. To determine the enantiomer purity, the precipitated protein was separated and the organic phase was derivatized with trifluoroacetic acid anhydride (TFAA). One sample was analyzed by chiral gas chromatography.

Separating conditions of the GC:

Column: Lipodex E (25m×0.25mm ID)

Helium: 0.8 bar

Hydrogen: 0.5 bar

Sample Volume: 1 μl $T_{col}$: 80° C. or 90° C., respectively '$T_{injector}$: 260° C.

Figure 6A:
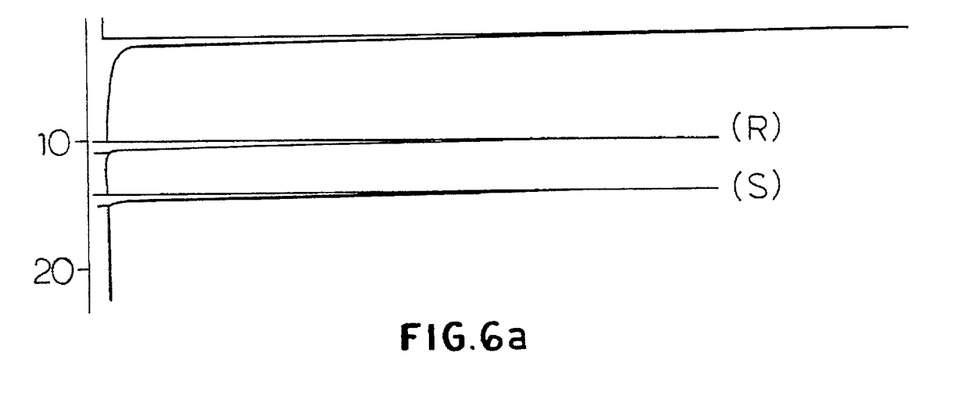
FIGS. 6a and 6b are comparative chromtographs showing the chromatographic separation of (R)- and (S) 3-hydroxybutyric acid methyl ester and indeed (a) for the racemic mixture (b) for the product obtained by KERed catalyzed conversion product according to the invention.
Figure 6B:
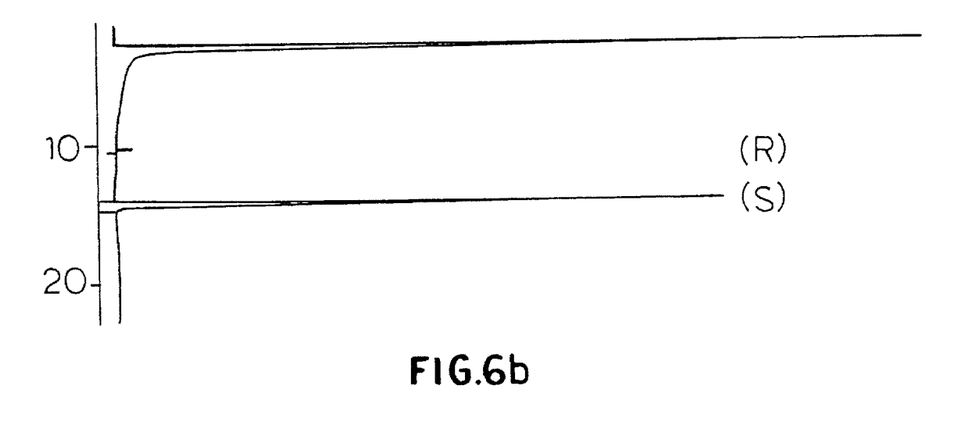

Retention times:

3-(R)-hydroxybutyric acid methyl ester 10.5 min 3-(S)-hydroxybutyric acid methyl ester 14.9 min The elution sequence of the enantiomers on the chiral GC column was determined with pure enantiomers of 3-hydroxybutyric acid methyl ester to be (R) before (S). The results of the GC analysis are shown in FIG. 6. The ketoester reductase from *Candida parapsilosis* converts 3-oxobutyric acid methyl ester with an enantiomer excess of 98% and a yield of 95% to (S)-3-hydroxybutyric acid methyl ester.

I. Enzyme Catalyzed production of 5-hydroxyhexanoic acid ethyl ester in batch conversion By analogy to example 3.H 5-oxohexanoic acid ethyl ester was enzymatically reduced in preparative scale. Samples were analyzed by means of chiral gas chromatography ($T_S$:90° C.).

Figure 7:
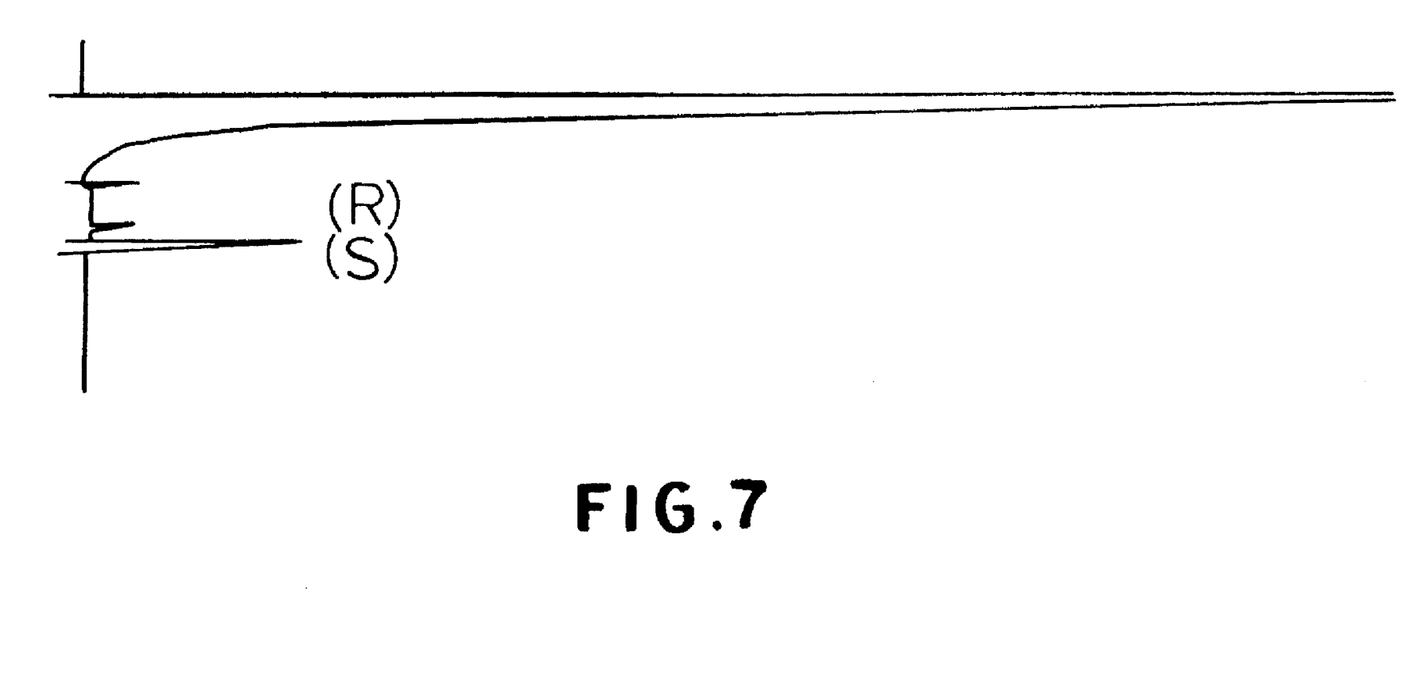
FIG. 7 is a chromatograph showing the chromatographic separation of (R)- and (S)- 3 hydroxybutyric acid ethyl ester or the KERed conversion product according to the invention.

Retention times:

5-(R)-hydroxyhexanoic acid ethyl ester: 25.0 min 5-(S)-hydroxyhexanoic acid ethyl ester: 26.9 min The results of the GC analysis is shown in FIG. 7. The ketoester reductase from *Candida parapsilosis* converts 5-oxohexanoic acid ethyl ester with an enantiomer excess of 95% and a yield of 96% to(S)-5-hydroxyhexanoic acid ethyl ester J. Proof of the Stereospecificity of the Enzyme For proof of the stereospecificity of the enzyme and the enantiomer purity of the products, two methods were used. On the one hand enzymatically produced product was investigated with a chiral gas chromatography capable to separate the (R)- and (S)-hydroxy esters from one another and on the other hand the oxidation reaction was measured photometrically using commercially obtained pure isomers of R and S-hydroxy compounds.

1. Chiral GC isomers of R and S- hydroxy

The products of the enzymatic conversion as well as the purchased pure enantiomers were separated by gas chromatography on the chiral phase analogous to Example 3.H. The matching of the peaks was effected by comparison with the commercial pure enantiomers of 3-hydroxybutyric acid methyl ester. The elution sequence (R) before (S) applies for the homologous series of the hydroxyester. FIG. 6 shows that one can arrive by enzymatic conversion at pure (S) hydroxybutyric acid methyl ester.

2. Reverse reaction with (R)- or (S)-Hydroxy Compounds

For the photometric proof of stereospecificity the following test compositions were carried out.

| | | |
|---|---|---|
| I) | 35 mM | (R)-hydroxybutyric acid methyl ester |
| | 0.5 mM | NAD |
| | 10 μl | enzyme solution |
| | TRIS-HCl-buffer | pH 9, 0.1 M |
| II) | 35 mM | (S)-hydroxybutyric acid methyl ester |
| | 0.5 mM | NAD |
| | 10 μl | enzyme solution |
| | TRIS-HCl-buffer | pH 9, 0.1 M |
| | Temperature: | 56° C. |
| III) | 8 mM | (R)-phenylethanol |
| | 0.5 Mm | NAD |
| | 10 μl | enzyme solution |
| | TRIS-HCl-buffer | pH 9, 0.1 M |
| IV) | 8 mM | (S)-phenylethanol |
| | 0.5 mM | NAD |
| | 10 μl | enzyme solution |
| | TRIS-HCl-buffer | pH 9, 0.1 M |

The activity measurement was carried out photometrically at 340 nm.

| Results | |
|---|---|
| Composition I: 7% | Composition II: 100 |
| Composition III: 1.1% | Composition IV: 100% |

These results indicate clearly that the enzyme is highly specific for (S)-3-hydroxybutyric acid methyl ester and (S)-phenylethanol.

What is claimed is:

1. A process for producing a keto ester reductase suitable for NADH dependent enzymatic conversion of beta-, gamma-, or delta-keto acid esters to corresponding optically active S- beta-, gamma-, or delta-hydroxy acid esters, which comprises the steps of:

(a) cultivating a microorganism selected from the group consisting of *Candida parapsilosis, Yarrowinia cellobiosa, Rhodococcus erythropolis,* and *Pseudomonas acidovorans* to form the keto ester reductase, said keto ester reductase having the following characteristics in purified form:

molecular weight 136 kDa±11kDa as determined by gel permeation chromatography on Sephadex G-200;

a pH optimum for conversion of the keto ester to the hydroxy acid esters between pH 7.8 and 8.0 and for the reverse reaction of converting the acid esters to the keto esters at a pH optimum of 9.5;

a temperature optimum between 36 and 40 degrees C. for conversion of the keto esters to the hydroxy acid esters and from 50 to 56 degrees C. for the reverse reaction of converting the acid esters to the keto esters;

rapid deactivation by Hg2+, Pb2+, Ag+, Cu2+, Ni2+, Sn2+, and Co2+, strong inhibition by p-hydroxymercuribenzoate 5,5'-dithio-bis-(2-nitrobenzoate), iodoacetamide, 2,2'-bipyridyl and o-phenanthroline, and stabilized by an SH-protecting agent;

reduces aliphatic, alicyclic, and aromatic ketones, diketones, ketals, and aldehydes and oxidizes primary and secondary alcohols;

(b) extracting the keto ester reductase from the microorganism to form a crude cell extract; and (c) isolating the keto ester reductase from the crude cell extract.

2. The process for producing a keto ester reductase defined in claim 1 wherein the microorganism is *Candida parapsilosis* DSM 70 125.

3. The process for producing a keto ester reductase defined in claim 1 which further comprises the steps of chromatographically separating the keto ester reductase obtained in step (c) for further purification of the keto ester reductase.

4. The process for producing a keto ester reductase defined in claim 1 wherein in step (a) said microorganism is cultivated on a medium containing a long chain alkanoic acid or an alkane as a carbon source.

5. A isolated keto ester reductase suitable for NADH-dependent enzymatic conversion of beta-, gamma- or delta-keto acid esters to the corresponding optically active S-beta-, gamma- or delta-hydroxy acid esters obtained from a microorganism selected from the group consisting of *Candida parapsilosis, Yarrowinia cellobiosa, Rhodococcus erythropolis,* and *Pseudomonas acidovorans,* said keto ester reductase having the following characteristics in purified form:

molecular weight 136 kDa±11kDa as determined by gel permeation chromatography on Sephadex G-200;

a pH optimum for conversion of the keto ester to the hydroxy acid esters between pH 7.8 and 8.0 and for the reverse reaction of converting the acid esters to the keto esters at a pH optimum of 9.5;

a temperature optimum between 36 and 40 degrees C. for conversion of the keto esters to the hydroxy acid esters and from 50 to 56 degrees C. for the reverse reaction of converting the acid esters of the keto esters;

rapid deactivation by Hg2+, Pb2+, Ag+, Cu2+, Ni2+, Sn2+, and Co2+, strong inhibition by p-hydroxymercuribenzoate 5,5'-dithio-bis-(2-nitrobenzoate), iodoacetamide, 2,2'-bipyridyl and o-phenanthroline, and stabilized by an SH-protecting agent; and reduces aliphatic, alicyclic, and aromatic ketones, diketones, ketals, and aldehydes and oxidizes primary and secondary alcohols.

6. The keto ester reductase defined in claim 5 isolated from *Candida parapsilosis* DSM 70125.

7. A method for enzymatic conversion of beta-, gamma- or delta-keto acid esters to the corresponding optically active S- beta-, gamma- or delta-hydroxy acid esters which comprises the step of contacting the keto acid esters with the keto ester reductase defined in claim 5 in the presence of NADH.

8. A method of producing an optically active R-beta-, gamma-, or delta-hydroxy acid ester from a racemate containing the R-hydroxy acid ester and the corresponding S-hydroxy acid ester which comprises the steps of (a) selectively oxidizing the corresponding S-hydroxy acid ester in the racemic mixture by contacting the racemic mixture with the keto ester reductase defined in claim 5 to form a beta-, gamma- or delta-keto acid ester while leaving behind the corresponding optically active R-hydroxy acid ester; and (b) separating the beta-, gamma- or delta-keto acid ester from the R-hydroxy acid ester.

* * * * *